United States Patent [19]

Lovell

[11] 4,087,523
[45] May 2, 1978

[54] INSECTICIDAL PYRETHROID COMPOSITIONS

[75] Inventor: James Byron Lovell, Pennington, N.J.

[73] Assignee: American Cyanamid Company, Stamford, Conn.

[21] Appl. No.: 623,864

[22] Filed: Oct. 20, 1975

[51] Int. Cl.$^2$ .......................... A01N 9/02; A01N 9/20; A01N 9/30; A01N 9/36
[52] U.S. Cl. .................................... 424/218; 424/200; 424/213; 424/300; 424/304; 424/305; 424/306; 424/308; 424/326; 424/352
[58] Field of Search ................ 424/218, 304, 326, 352

[56] References Cited

U.S. PATENT DOCUMENTS

| | | | |
|---|---|---|---|
| 3,502,720 | 3/1970 | Arndt | 260/564 |
| 3,966,959 | 6/1976 | Addor | 424/304 |

OTHER PUBLICATIONS

Chem. Week, Jun. 21, 1972.
Pesticide Index, 4th Ed., 1969, Frear, pp. 285 & 372.

*Primary Examiner*—Allen J. Robinson
*Attorney, Agent, or Firm*—H. G. Jackson

[57] ABSTRACT

This invention relates to novel insecticidal compositions comprising a m-phenoxybenzyl ester of a spirocarboxylic acid and an insecticidal agent of chlorinated camphene; 0,0-dimethyl-0-p-nitrophenyl phosphorothioate; N'-(4-chloro-o-tolyl)-N,N-dimethylformamidine; 2-(diethoxy-phosphinylimino)-4-methyl-1,3-dithiolane; 0,0-dimethyl-S-[4-oxo-1,2,3-benzotriazin-3-(4H)-ylmethyl]phosphorodithioate; 1-naphthyl N-methylcarbamate, 0,0-dimethylphosphorodithioate of diethylmercaptosuccinate; or mixtures of the latter named chemical insecticidal agents and to the use of the above compositions for protecting agricultural crops from attack by insect pests.

9 Claims, No Drawings

INSECTICIDAL PYRETHROID COMPOSITIONS

BACKGROUND OF THE INVENTION

1. Field of the Invention

The field of the invention is pyrethroids in combination with selected insecticidal agents for the control of insect pests, particularly those which are of major economic importance to the cotton industry.

2. The Prior Art

Pyrethrin-like compounds (pyrethroids) are known in the chemical art. Many such compounds have been shown to possess insecticidal properties, but most have failed to provide entirely satisfactory insect and/or acarina control. None, to the best of our knowledge, has been entirely satisfactory for the control of the complex of insects which ravage growing cotton plants: and, with few exceptions, all have been subject to extremely rapid degradation to non-toxic substances. This latter property has been recognized as a major deficiency of the pyrethroids. While such compounds have provided excellent knockdown of many insects, rapid degradation of said compounds has resulted in lack of residual insect control even for a few days.

The pyrethroids useful in my invention are described in the R. W. Addor U.S. patent application Ser. No. 550,105, filed Feb. 13, 1975, now U.S. Pat. No. 3,966,959 (1976).

Heretofore, many conventional insecticidal chemicals have also been employed for the control of insects which ravage growing cotton plants. Many have met with a high degree of acceptance by cotton growers, but virtually all have been found to have their limitations and none has afforded complete protection for the growing cotton plants against the insect complex encountered.

It is therefore an object of the present invention to provide an insecticidal composition which is highly effective for protecting crops, particularly cotton crops, from insect attack.

It is also an object of this invention to provide a chemical composition which contains (1) a pyrethroid compound that is not subject to immediate degradation and (2) a selected phosphate, N-methylcarbamate, chlorinated camphene or chlorinated formamidine insecticide; and it is a further object of this invention that such composition be more effective for controlling certain Lepidopterous, Hemipterous and Coleopterous insects and more effective for protecting important agronomic crops from attack by the insects, than is the pyrethroid alone or the phosphate, carbamate, chlorinated camphene, chlorinated formamidine or mixtures thereof.

Advantageously, the compositions of the invention are useful as contact or stomach posions. They are superior in insecticidal activity or insect repellancy, to the pyrethroid alone or the phosphate, carbamate, chlorinated camphene or chlorinated formamidine insecticides and can be employed as protecting agents for important agronomic crops such as cotton, soybeans, tobacco, cole crops, leafy vegetables, forage crops, corn, snapbeans, and tomatoes.

SUMMARY OF INVENTION

This invention relates to insecticidal compositions comprising (a) a phenoxybenzyl ester of a spirocarboxylic acid having a formula of:

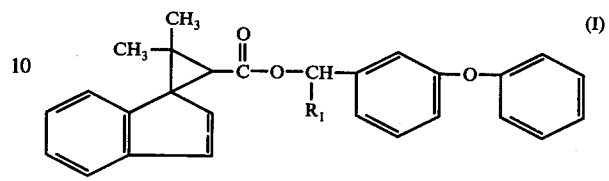

or

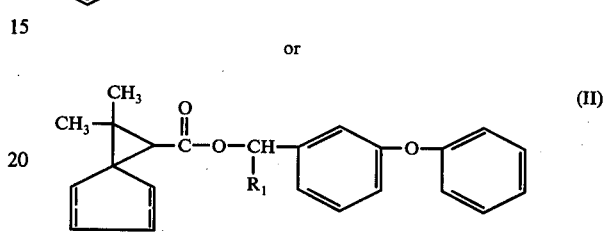

wherein $R_1$ is hydrogen, cyano or ethylnyl, === represents a single or double bond, and the optical and geometric isomers thereof, and (b) chlorinated camphene; O,O-dimethyl-O-p-nitrophenyl phosphorothioate; N'-(4-chloro-o-tolyl)-N,N-dimethylformamidine; 2-(diethoxyphosphinylimino)-4-methyl-1,3-dithiolane; O,O-dimethyl S-[4-oxo-1,2,3-benzotriazin-3-(4H)ylmethyl]-phosphorodithioate; O,O-dimethylphosphorodithioate of diethylmercaptosuccinate; 1-naphthyl N-methylcarbamate, and mixtures thereof. More particularly, this invention relates to novel insecticidal compositions in which the ratio of the conventional insecticide to the pyrethroid is from 5:4 to 40:1 and preferably 5:4 to 20:1. Still more particularly, the compositions of this invention are applied to foliage of plants, which are to be protected from insect attack, in amounts sufficient to provide from about 1.0 to 5.0 oz and preferably 1.6 to 3.2 oz of the pyrethroid and from 0.25 to 4.0 lbs per acre of the conventional insecticide. These most preferred rates are equivalent to 0.11 to 0.22 kg/hectare of the pyrethroid and from 0.28 to 4.48 kg/hectare of the conventional insecticide.

DESCRIPTION OF THE PREFERRED EMBODIMENTS

In accordance with this invention the phenoxybenzyl esters of benzospirocarboxylic acids depicted by formula I, can be prepared by reacting approximately equimolar amounts of an acid halide, preferably the chloride, of a benzospirocarboxylic acid (IV) and m-phenoxybenzyl alcohol (V). The reaction is generally conducted in the presence of a suitable solvent such as benzene, toluene, diethyl ether, or the like, at a temperature between about 10° C and 30° C, and in the presence of an acid acceptor such as an organic tertiaryamine such as triethylamine, trimethylamine, pyridine, or the like. The reaction can be graphically illustrated as follows:

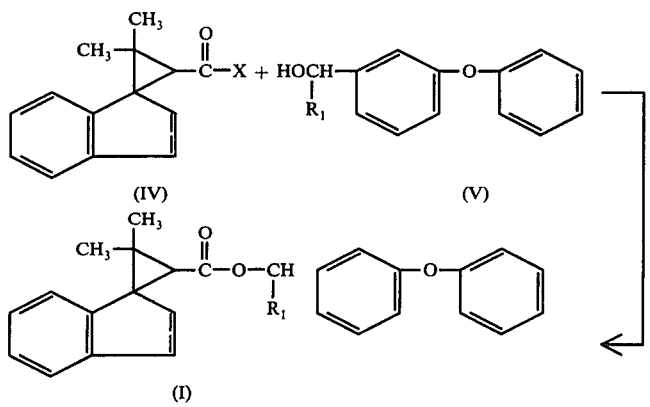

(IV)  (V)

(I)

wherein $R_1$ is hydrogen, cyano, or ethynyl, and X is halogen, preferably chloro.

The benzospirocarboxylic acid halide (IV) is readily obtained by reaction of the appropriate benzospirocarboxylic acid (III) with a thionyl halide such as thionyl chloride, thionyl bromide or a phosphorus halide such as phosphorus trichloride or phosphorus pentachloride in the presence of an organic solvent such as toluene, benzene or benzenehexane mixture. This reaction may be conducted at room temperature but is preferably conducted at 60°–90°; and can be illustrated as follows:

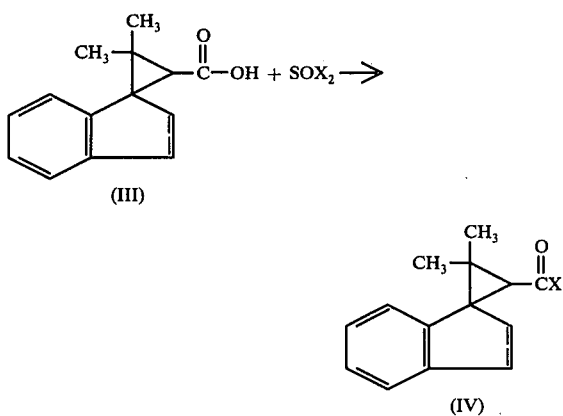

(III)

(IV)

The formula II phenoxybenzyl esters of spirocarboxylic acids can be prepared in a manner similar to that described above for the preparation of the formula I benzospiro compounds, by substituting the appropriate spirocarboxylic acid (VI) for the above-mentioned benzospirocarboxylic acid (III); converting said acid to its corresponding acid halide (VII) and reacting the thus-formed acid halide with m-phenoxybenzyl alcohol (V), under the conditions mentioned above, to obtain the formula (II) m-phenoxybenzyl ester of the spirocarboxylic acid. This reaction can be graphically illustrated as follows:

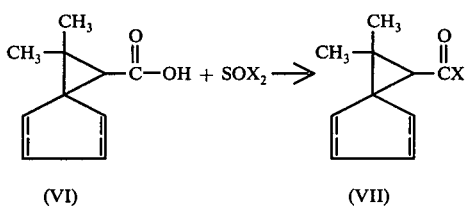

(VI)  (VII)

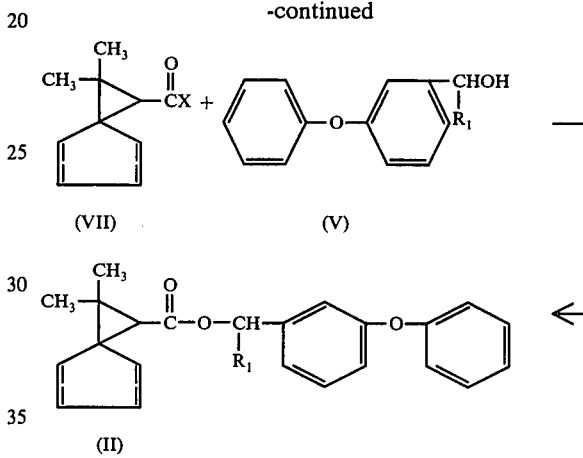

(VII)  (V)

(II)

wherein X is halogen, preferably chloro, and $R_1$ is hydrogen, cyano, or ethynyl.

In accordance with this invention, it should also be understood that various geometric isomers as well as optical isomers of the above-identified compounds do result from the preparations described. For example, in the synthesis of the 2,2-dimethylspiro[2,4]hepta-4,6-diene-1-carboxylic and 2,2-dimethylspiro[2,4]hepta-4-ene-1-carboxylic acid esters of m-phenoxybenzyl alcohol, d and l isomeric pairs are formed. In the preparation of the α-cyano- and α-ethynyl-m-phenoxybenzyl esters, an additional chiral center is introduced, and this allows for additional d, l pairs. Additionally, the esters derived from 2,2-dimethyl-4,5-benzo spiro[2,4]hepta-4,6-diene-1-carboxylic acid and 2,2-dimethyl-4,5-benzospiro[2,4]hepta-4-ene-1-carboxylic acid will be further complicated by the presence of cis and trans isomers.

For the control of insects, including soil insects, which attack growing plants and/or harvested crops, including stored grain, the insecticidal compositions of this invention may be applied to the foliage of plants the insect's habitat and/or the insect's food supply. Generally, the active composition is applied in the form of a dilute liquid spray; however, it may also be applied as an aerosol, a dust, wettable powder, or the like.

Liquid sprays which are particularly useful are oil sprays and emulsifiable concentrates which can be further diluted for application.

A typical emulsifiable concentrate useful for protecting a variety of crops such as cereals, cole crops, cucurbits, ornamentals, shrubs, and the like, may comprise about 24% by weight of the active composition; 4% by weight of an emulsifying agent, conventionally employed in the preparation of pyrethroid formulations: 4% by weight of a surfactant; 23% by weight of an organic solvent such as cyclohexanone; and about 45% by weight of a petroleum solvent having a minimum aromatic content of about 93 volume %.

Typical compositions of this invention which are highly effective for controlling insect pests and or protecting crops from attack thereby are as follows.

Typical Preferred Compositions of the Present Invention

| Chemical | Rate of Chemical kg/ha | *Pyrethroid Rate kg/ha | Ratio of Chemical To Pyrethroid |
|---|---|---|---|
| Chlorinated Camphene | 2.24–4.48 | 0.11–0.22 | 10–1 to 40–1 |
| Methyl Parathion | 0.28–1.68 | 0.11–0.22 | 5–4 to 15–1 |
| Chlorinated Camphene + Methyl Parathion | 0.56 to 4.48– 0.28 to 1.68 | 0.11–0.22 | 5–4–1 to 40–15–1 |
| Chlordimeform | 0.56–1.12 | 0.11–0.22 | 2.5–1 to 10–1 |
| Chlorinated Camphene + Chloridimeform | 2.2–0.14 | 0.11–0.22 | 10–0.625–1 to 20–1.25–1 |
| Chlorinated Camphene + Methyl Parathion + Chlordimeform | 2.2–0.56–0.14 | 0.11–0.22 | 10–2.5–0.625–1 to 20–5–1.25–1 |
| Carbaryl | 1.12–2.8 | 0.11–0.22 | 5–1 to 25–1 |
| Azinphos-methyl | 0.28–0.56 | 0.11–0.22 | 5–4 to 5–1 |
| Malathion | 0.56–2.2 | 0.11–0.22 | 2.5–1 to 20–1 |

*Preferred pyrethroids are 2,2-Dimethyl-4,5-benzospiro[2,4]hepta-4,6-diene-1-carboxylic acid, m-phenoxybenzyl ester and 2,2-Dimethyl-4,5-benzospiro[2,4]hepta-4,6-diene-1-carboxylic acid, α-cyano-m-phenoxybenzyl ester.

The invention is further demonstrated by the non-limiting examples provided below.

EXAMPLE 1

Preparation of 2,2-Dimethyl-4,5-benzospiro[2,4]hepta-4,6-diene-1-carboxylic acid, m-phenoxybenzyl ester

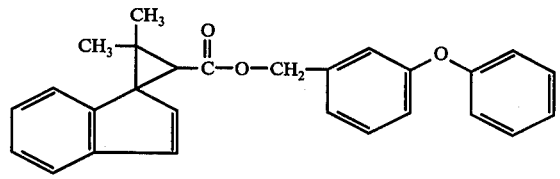

To 4.3 g (0.02 mole) of 2,2-dimethyl-4,5-benzospiro-2,4-hepta-4,6-diene-1-carboxylic acid in either hexane/benzene or benzene is added 8 ml of thionyl chloride. The solution is then stirred for 12 hours at room temperature. The solvent is then removed in vacuo leaving 4.7 g of an orange liquid (theoretical yield). Infrared indicates an acid chloride carbonyl at 1790 cm$^{-1}$.

The acid chloride and 4.0 g (0.02 mole) of m-phenoxy benzyl alcohol are dissolved in 20 ml of ether, and 2.1 g (0.02 mole) of triethylamine dissolved in 8 ml of ether is added dropwise at 20° C. Solids precipitate from solution immediately. The resulting mixture is stirred for 12 hours at room temperature. The crude product is partitioned in an ether/water mixture, and the ether layer is dried over magnesium sulfate and concentrated in vacuo to yield 7.7 g (96% theory) of a brown liquid.

The crude product is purified by dry-column chromatography on silica gel using 25% methylene chloride in hexane as a solvent. 4.4 Grams of a pale yellow liquid is obtained. The infrared spectrum shows an ester carbonyl band at 1720 cm$^{-1}$. The nuclear magnetic resonance spectrum (CCl$_4$) shows the following: δ = 1.41, 1.45, 1.58, 1.66 (4S, 6H, methyls), 2.61 (S, 1H, cyclopropane H), 4.85–5.10 (M, 2H, O—CH$_2$), 6.12 (d, 0.5H, J = 5.5 Hz, vinyl), 6.66–7.76 (m, 14.5H aromatic and vinyl).

Analyses: Calculated for C$_{27}$H$_{24}$O$_3$: C, 81.83; H, 6.06. Found: C, 82.14; H, 6.29.

EXAMPLE 2

Preparation of 2,2-Dimethyl-4,5-benzospiro[2,4]hepta-4,6-diene-1-carboxylic acid, α-cyano-m-phenoxybenzyl ester

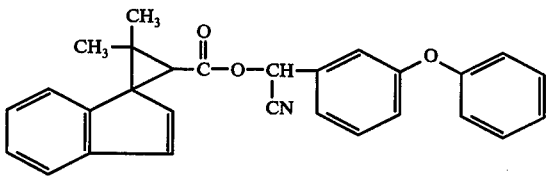

2,2-Dimethyl-4,5-benzospiro [2,4]hepta-4,6-diene-1-carboxylic acid, 3.4 g, is dissolved in 100 ml of a hexane/benzene (4:1) solution. Thionyl chloride, 15.0 g, is then added and the solution is stirred for 12 hours. Refluxing is carried out for 20 minutes, and the volume is reduced in vacuo to remove solvents and excess thionyl chloride. The acid chloride is used directly without further purification. The acid chloride is taken up in 20 ml of benzene and is added dropwise to a solution of 3.1 g of α-cyano-m-phenoxybenzyl alcohol and 1.0 g of pyridine in 100 ml of benzene. After 4 hours, the precipitate is filtered, and the filtrate reduced in vacuo to give a viscous oil. Purification by column chromatography on silica gel with elution by chloroform/hexane (1:2) gives 1.3 g of pale yellow oil which exhibits the following spectral properties: infrared spectrum (neat film) 1730 cm$^{-1}$; nuclear magnetic resonance spectrum (CDCl$_3$) δ = 6.8–7.6 (m, 14.5H, aromatic and vinyl), 6.37

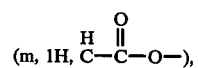

6.22 (d, 0.5H, vinyl), 2.73

(m, 1H, H–C(=O)–O–), 1.72–1.43 (m, 6H, methyls).

EXAMPLE 3

Preparation of 2,2-Dimethyl-4,5-benzospiro[2,4]hepta-4-ene-1-carboxylic acid, m-phenoxybenzyl ester The procedure of Example 1 is followed using 2,2-dimethyl-4,5-benzospiro[2,4]hepta-4-ene-1-carboxylic acid in place of 2,2-dimethyl-4,5-benzospiro[2,4]hepta-4,6-diene-1-carboxylic acid to give the crude product as an oil. The pure ester obtained by chromatography had the following spectral properties: Infrared spectrum (heat film) 1720 cm$^{-1}$; nuclear magnetic resonance spectrum (CCl$_4$) δ = 6.7–7.6 (m, 13H, aromatic), 4.8–51 (m, 2H, O—CH$_2$), 1.1–3.2 (m, 11H, CH$_3$, indane CH$_2$, and cyclopropane H).

EXAMPLE 4

Preparation of 2,2-Dimethyl-4,5-benzospiro[2,4]hepta-4-ene-1-carboxylic acid, α-cyano-m-phenoxybenzyl ester The procedure of Example 2 is followed using 2,2-dimethyl-4,5-benzospiro[2,4]hepta-4-ene-1-carboxylic acid in place of 2,2-dimethyl-4,5-benzospiro[2,4]hepta-4,6-diene-1-carboxylic acid to give the crude product.

EXAMPLE 5

Preparation of 2,2-Dimethylspiro[2,4]hepta-4,6-diene-1-carboxylic acid, m-phenoxybenzyl ester The procedure of Example 1 is followed using 2,2-dimethyl[2,4]hepta-4,6-diene-1-carboxylic acid in place of 2,2-dimethyl-4,5-benzospiro[2,4]hepta-4,6-diene-1-carboxylic acid to give the crude product.

EXAMPLE 6

Preparation of 2,2-Dimethylspiro[2,4]hepta-4,6-diene-1-carboxylic acid, α-cyano-m-phenoxybenzyl ester The procedure of Example 2 is followed using 2,2-dimethylspiro[2,4]hepta-4,6-diene-1-carboxylic acid in place of 2,2-dimethyl-4,5-benzospiro[2,4]hepta-4,6-diene-1-carboxylic acid to give the crude product.

EXAMPLE 7

Preparation of 2,2-Dimethylspiro[2,4]heptane-1-carboxylic acid, m-phenoxybenzyl ester

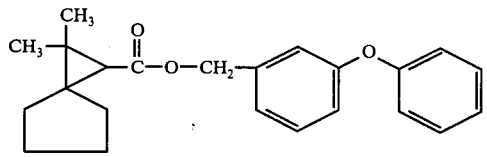

The procedure of Example 1 is followed using 2,2-dimethylspiro[2,4]heptane-1-carboxylic acid in place of 2,2-dimethyl-4,5-benzospiro[2,4]hepta-4,6-diene-1-carboxylic acid to give the crude product. The pure ester obtained by chromatography has the following spectral properties: Infrared spectrum (neat film) 1730 cm$^{-1}$; nuclear magnetic resonance spectrum (CCl$_4$) δ = 6.8–7-4 (m, 9H, aromatic), 5.0 (s, 2H, O—CH$_2$), 1.4–1.7 (m, 8H, cyclopentane CH$_2$), 1.1 (s. 3H, CH$_3$), 1,2 (s, 3H, CH$_3$).

EXAMPLE 8

Preparation of 2,2-Dimethylspiro[2,4]heptane-1-carboxylic acid, α-cyano-m-phenoxybenzyl ester The procedure of Example 2 is followed using 2,2-dimethylspiro[2,4]heptane-1-carboxylic acid in place of 2,2-dimethyl-4,5-benzospiro[2,4]hepta-4,6-diene-1-carboxylic acid to give the crude product.

It must be recognized that various geometric isomers as well as optical isomers result from these preparations. Thus, in the case of the 2,2-dimethylspiro[2,4]hepta-4,6-diene-1-carboxylic acid and 2,2-dimethylspiro[2,4]-heptane-1-carboxylic acid esters of m-phenoxybenzyl alcohol, d and l isomeric pairs will result. Where the α-cyano and α-ethynyl m-phenoxybenzyl esters are formed, an additional chiral center is introduced allowing for additional d, l pairs. Although in most instances the separation of these isomers may not be practical, it is recognized that they will differ in the degree of effectiveness and the spectrum of their activity against the many insects and other pests of economic importance. In addition, the subject esters derived from 2,2-dimethyl-4,5-benzospiro[2,4]hepta-4,6-diene-1-carboxylic acid and 2,2-dimethyl-4,5-benzospiro[2,4]-hepta-4-ene-1-carboxylic acid will be further complicated by the presence of cis and trans isomers. These different esters are also expected to show differing degrees of insecticidal activity when separately tested.

EXAMPLE 9

Preparation of 2,2-Dimethyl-4,5-benzospiro[2,4]hepta-4,6-diene-1-carboxylic acid, α-ethynyl-m-phenoxybenzyl ester The procedure of Example 1 is followed using α-ethynyl-m-phenoxybenzyl alcohol in place of m-phenoxybenzyl alcohol to give the product as an oil.

EXAMPLE 10

Preparation of 2,2-Dimethyl-4,5-benzospiro[2,4]hepta-4-ene-1-carboxylic acid, α-ethynyl-m-phenoxybenzyl The procedure of Example 1 is followed using 2,2-dimethyl-4,5-benzospiro[2,4]hepta-4-ene-1-carboxylic acid in place of 2,2-dimethyl-4,5-benzospiro[2,4]hepta-4,6-diene-1-carboxylic acid and α-ethynyl-m-phenoxybenzyl alcohol in place of m-phenoxybenzyl alcohol to give the product as an oil.

EXAMPLE 11

Preparation of 2,2-Dimethylspiro[2,4]hepta-4,6-diene-1-carboxylic acid, α-ethynyl-m-phenoxybenzyl ester The procedure of Example 1 is followed using 2,2-dimethylspiro[2,4]hepta-4,6-diene-1-carboxylic acid in place of 2,2-dimethyl-4,5-benzospiro[2,4]hepta-4,6-diene-1-carboxylic acid and α-ethynyl-m-phenoxybenzyl alcohol in place of m-phenoxybenzyl alcohol to give the product as an oil.

EXAMPLE 12

Preparation of 2,2-Dimethylspiro[2,4]heptane-1-carboxylic acid, α-ethynyl-m-phenoxybenzyl ester The procedure of Example 1 is followed using 2,2-dimethylspiro[2,4]heptane-1-carboxylic acid in place of 2,2-dimethyl-4,5-benzospiro[2,4]hepta-4,6-diene-1-carboxylic acid and α-ethynyl-m-phenoxybenzyl alcohol in place of m-phenoxybenzyl alcohol to give the product as an oil.

EXAMPLE 13

Evaluation of Chemical Compositions Against Tobacco Budworm (Heliothis virescens) on Cotton Plants The effectiveness of the compositions of this invention for protecting cotton plants, and/or controlling insects which attack them, is demonstrated by the following tests.

In these tests stock solutions of test compounds are prepared by dissolving and/or dispersing a sufficient amount of test compound in 67 ml of acetone and diluting the thus prepared solution with 36 ml of water to yield 100 ml of stock solution with a given concentration of test compound. Thus, 400 mg of N'-(4-chloro-2-methylphenyl)-N,N-dimethylformamidine yields a stock solution containing 4,000 ppm of compound; and this solution, when used with equal parts of three additional stock solutions, provides an insecticidal composition containing 1,000 ppm of the above-said compound. All stock solutions of test compounds are prepared in this manner and solutions are varied in concentration to match the desired ratio among components.

To determine the effectiveness of test compositions for controlling the tobacco budworm (Heliothis virescens (Fabricius)) and protecting cotton plants from attack thereby, one-third of a cotyledon of a Stoneville #213 cotton plant, which had been dipped in test solution, is placed in a 1 oz plastic medicine cup containing a 1 inch dental wick saturated with water. One third-instar tobacco budworm larva is placed in each cup and the cup capped and held at 26° C and 30% relative humidity. Ten larvae are used for each concentration tested. After 3 days, mortality counts are made. Data obtained are reported below.

For convenience in reporting data obtained in this evaluation and/or evaluations reported in subsequent examples, common names for chemicals other than the pyrethroids are used. Said chemicals are as follows:

| Chemical | Common Name |
| --- | --- |
| Chlorinated camphene | toxaphene |
| O,O-Dimethyl-S-[4-oxo-1,2,3-benzotriazin-3(4H)-ylmethyl]-Phosphorodithioate | azinphos-methyl |
| N'-(4-Chloro-2-methylphenyl)-N,N-dimethylformamidine | chlordimeform |

-continued

| Chemical | Common Name |
| --- | --- |
| O,O-Dimethyl-O-p-nitrophenyl phosphorothioate | methyl parathion |
| 2-(Diethoxyphosphinylimino)-4-methyl-1,3-dithiolane | mephosfolan |
| O,O-Dimethyl phosphorodithioate of diethylmercaptosuccinate | malathion |
| 1-Naphthyl N-methylcarbamate | carbaryl |

Table I

Control of Tobacco Budworm Larvae on Cotton Plants Expressed as Percent Mortality of Larvae

| Compound | Concentration ppm | % Mortality |
| --- | --- | --- |
| 2,2-Dimethyl-4,5-benzospiro[2,4]hepta-4,6-diene-1-carboxylic acid, m-phenoxybenzyl ester | 15 | 10 |
|  | 30 | 33 |
| 2,2-Dimethyl-4,5-benzospiro-[2,4]hepta-4,6-diene-1-carboxylic acid, α-cyano-m-phenoxybenzyl ester | 30 | 38 |
| Chlorinated camphene | 100 | 0 |
| Chlordimeform | 1000 | 50 |
| Azinphos-methyl | 50 | 0 |
| Chlorinated camphene plus 2,2-Dimethyl-4,5-benzospiro[2,4]hepta-4,6-diene-1-carboxylic acid, m-phenoxybenzyl ester | 100 plus 30 | 50 |
| Chlorinated camphene plus 2,2-Dimethyl-4,5-benzospiro[2,4]hepta-4,6-diene-1-carboxylic acid, α-cyano-m-phenoxybenzyl ester | 60 plus 3 | 100 |
| Azinphos-methyl plus 2,2 Dimethyl-4,5-benzospiro[2,4]hepta-4,6-diene-1-carboxylic acid, α-cyano-m-phenoxybenzyl ester | 50 plus 15 | 80 |

EXAMPLE 14

Evaluation of Chemical Compositions Against Cabbage Looper (Trichoplusia ni) larvae on Cotton Plants To determine the effectiveness of test compositions for controlling cabbage looper (Trichoplusia ni (Huber)) on cotton plants true leaves of a Stoneville #213 cotton plant, dipped in test solution and dried, are placed in separate 9.0 cm petri dishes which are fitted with a moist Whatman #1 filter paper. Ten third-instar cabbage looper larvae are placed in each of the dishes which are then covered and held in a room maintained at 26° C and 30% relative humidity. After 3 days, mortality counts are made and feeding damage is estimated. Data obtained are reported below.

Table II

Control of Cabbage Looper Larvae on Cotton Plants Expressed as Percent Mortality and Plant Protection Expressed as Percent Feeding Damage

| Compound or Composition | Concentration ppm | % Mortality | % Feeding Damage |
| --- | --- | --- | --- |
| 2,2-Dimethyl-4,5-benzospiro]2,4]-hepta-4,6-diene-1-carboxylic acid, m-phenoxybenzyl ester | 5 | 20 | 30 |
|  | 3 | 15 | 63 |
|  | 1.5 | 0 | 100 |
| 2,2-Dimethyl-4,5-benzospiro[2,4]-hepta-4,6-diene-1-carboxylic acid, α-cyano-m-phenoxybenzyl ester | 1.5 | 60 | 10 |
|  | 1 | 68 | 16 |
| Chlorinated camphene | 100 | 0 | 100 |
| Methyl parathion | 10 | 0 | 100 |
| Chlordimeform | 1000 | 40 | 100 |
| Azinphos-methyl | 150 | 0 | 100 |
| 2-(diethoxyphosphinylimino)-4-methyl-1,3-dithiolane | 100 | 50 | 100 |
| 2,2-Dimethyl-4,5-benzospiro[2,4]hepta-4,6-diene-1-carboxylic acid, m-phenoxybenzyl ester plus methyl parathion | 3 plus 10 | 70 | 10 |
| 2,2-Dimethyl-4,5-benzospiro[2,4]-hepta-4,6-diene-1-carboxylic acid, m-phenoxybenzyl ester Plus Methyl parathion Plus Chlordimeform Plus Chlorinated camphene | 1 Plus 15 Plus 1.875 Plus 30 | 90 | 2 |

Table II-continued
Control of Cabbage Looper Larvae on Cotton Plants Expressed as Percent Mortality and Plant Protection Expressed as Percent Feeding Damage

| Compound or Composition | Concentration ppm | % Mortality | % Feeding Damage |
|---|---|---|---|
| 2,2-Dimethyl-4,5-benzospiro[2,4]hepta-4,6-diene-1-carboxylic acid, α-cyano-m-phenoxybenzyl ester Plus<br>Chlordimeform | 1<br>Plus<br>1000 | 100 | 1 |
| 2,2-Dimethyl-4,5-benzospiro[2,4]hepta-4,6-diene-1-carboxylic acid, m-phenoxybenzyl ester Plus<br>Chlordimeform Plus<br>Chlorinated camphene | 0.25<br>Plus<br>250<br>Plus<br>125 | 70 | 20 |
| 2,2-Dimethyl-4,5-benzospiro[2,4]hepta-4,6-diene-1-carboxylic acid, α-cyano-m-phenoxybenzyl ester Plus<br>Azinphos-methyl | 1.5<br>Plus<br>150 | 90 | 5 |
| 2,2-Dimethyl-4,5-benzospiro[2,4]hepta-4,6-diene-1-carboxylic acid, m-phenoxybenzyl ester Plus<br>Azinphos-methyl | 5<br>Plus<br>150 | 90 | 5 |
| 2,2-Dimethyl-4,5-benzospiro[2,4]hepta-4,6-diene-1-carboxylic acid, α-cyano-m-phenoxybenzyl ester Plus<br>2-(diethoxyphosphinylimino)-4-methyl-1,3-dithiolane | 1<br>Plus<br>100 | 90 | 5 |

EXAMPLE 15
Effectiveness of Chemical Compositions Against Adult Boll Weevils (*Anthonomus grandis*) on Cotyledons of Cotton Plants To determine the effectiveness of test compositions for controlling boll weevils and/or protecting plants from their attack, cotyledons from Stoneville #213 cotton plants are dipped in solutions of test compositions and then permitted to dry. After drying, these treated cotyledons are placed in individual 9.0 cm petri dishes with moist Whatman #1 filter papers on the bottom thereof. Ten adult boll weevils are then placed in each of the dishes and the dishes are covered and placed in a room maintained at 26° C and 30% relative humidity. After 3 days, mortality counts are made and the amount of feeding is estimated.

Data obtained are reported in the Table III below.

Table III
Effectiveness of Compositions for Controlling Adult Boll Weevils on Cotyledons of Cotton Plants

| Compound or Composition | Concentration ppm | % Mortality | % Feeding Damage |
|---|---|---|---|
| 2,2-Dimethyl-4,5-benzospiro[2,4]hepta-4,6-diene-1-carboxylic acid, m-phenoxybenzyl ester | 300<br>100 | 43<br>23 | 5<br>3 |
| Chlorinated camphene | 500<br>100 | 20<br>0 | 10<br>15 |
| 2,2-Dimethyl-4,5-benzospiro[2,4]hepta-4,6-diene-1-carboxylic acid, α-cyano-m-phenoxybenzyl ester | 100 | 32 | 3 |
| Methyl parathion | 3 | 20 | 25 |
| Chlordimeform | 1000 | 0 | 25 |
| Malathion | 100 | 30 | 30 |
| Chlorinated camphene plus 2,2-Dimethyl-4,5-benzospiro[2,4]hepta-4,6-diene-1-carboxylic acid, α-cyano-m-phenoxybenzyl ester | 100<br>Plus<br>100 | 50 | 0 |
| Methyl parathion plus 2,2-Dimethyl-4,5-benzospiro[2,4]hepta-4,6-diene-1-carboxylic acid, α-cyano m-phenoxybenzyl ester | 3<br>+<br>100 | 100 | 5 |
| Chlorinated camphene plus methyl parathion plus 2,2-Dimethyl-4,5-benzospiro[2,4]hepta-4,6-diene-1-carboxylic acid, m-phenoxybenzyl ester | 60<br>+<br>30<br>+<br>100 | 100 | 0 |
| Chlorinated camphene plus methyl parathion plus 2,2-Dimethyl-4,5-benzospiro[2,4]hepta-4,6-diene-1-carboxylic acid, α-cyano-m-phenoxybenzyl ester | 60<br>+<br>30<br>+<br>100 | 100 | 0 |
| Chlorodimeform plus 2,2-Dimethyl-4,5-benzospiro[2,4]hepta-4,6-diene-1-carboxylic acid, m-phenoxybenzyl ester plus chlorinated camphene | 1000<br>+<br>300<br>+<br>500 | 90 | 0 |
| Malathion plus 2,2-Dimethyl-4,5-benzospiro[2,4]hepta-4,6-diene-1-carboxylic acid, m-phenoxybenzyl ester | 100<br>+<br>300 | 80 | 0 |

EXAMPLE 16
Evaluation of Chemical Compositions for the Control of Western Potato Leaf Hopper (*Empoasca abrupta* Delong)

A treated primary leaf of a Sieva lima bean plant is placed in a 9.0 cm petri dish with moist Whatman #1 filter paper on the bottom. Approximately 3 to 10, second-instar nymphs are tapped from the culture plant into the test dish which is then covered. The dish is held at about 26° C and which is then covered. The dish is held at about 26° C and 30% relative humidity for 3 days and then mortality counts are made.

Data obtained are reported in Table IV below.

Table IV

Effectiveness of Test Compositions for Controlling Western Potato Leaf Hoppers

| Chemical or Composition | Concentration ppm | % Mortality |
|---|---|---|
| Chlorinated camphene | 30 | 15 |
| Methyl Parathion | 3 | 38 |
| Azinphos-methyl | 5 | 0 |
| 2,2-Dimethyl-4,5-benzospiro[2,4]hepta-4,6-diene-1-carboxylic acid, m-phenoxy benzyl ester | 10 | 46 |
| 2,2-Dimethyl-4,5-benzospiro[2,4]hepta-4,6-diene-1-carboxylic acid, α-cyano-m-phenoxybenzyl ester | 10 | 52 |
| Chlorinated camphene plus 2,2-dimethyl-4,5-benzospiro[2,4]hepta-4,6-diene-1-carboxylic acid, m-phenoxybenzyl ester | 30 + 10 | 85 |
| Chlorinated camphene plus 2,2-Dimethyl-4,5-benzospiro[2,4]hepta-4,6-diene-1-carboxylic acid, α-cyano-m-phenoxybenzyl ester | 10 + 3 | 100 |
| Chlorinated camphene plus Methyl Parathion plus Chlordimeform plus 2,2-Dimethyl-4,5-benzospiro[2,4]hepta-4,6-diene-1-carboxylic acid, m-phenoxybenzyl ester | 15 + 7.5 + 0.94 + 5 | 100 |
| Azinphos methyl plus 2,2-Dimethyl-4,5-benzospiro[2,4]hepta-4,6-diene-1-carboxylic acid, α-cyano-m-phenoxybenzyl ester | 1.5 + 5 | 100 |

EXAMPLE 17

Evaluation of Chemical Composition for the control of Bean Aphids (*Aphid fabae* Scopoli)

A two-inch square fiber pot containing a nasturtium plant which is infested with approximately 100 aphids 2 days prior to test initiation, is placed on a 4 rpm turntable located in an exhaust hood. The plant and aphids are sprayed directly with the test solution for 2 revolutions of the turntable with a DeVilbiss atomizer at 20 psi air pressure. The spray tip is held 6 to 8 inches from the plant during spraying and after spraying the pot with plant and aphids is laid on its side on a white enamel tray. One day after treatment the plants are examined and mortality counts are made. Data obtained are reported in Table V below.

Table V

**Effectiveness of Chemical Compositions for Controlling Bean Apids (*Aphid fabae* Scopoli)**

| Chemical or Composition | Concentration ppm | % Mortality |
|---|---|---|
| Chlorinated camphene | 30 | 30 |
| Methyl parathion | 1 | 50 |
| Chlorodimeform | 100 | 5 |
| Azinphos-methyl | 1.5 | 60 |
| Carbaryl | 1.0 | 0 |
| 2,2-Dimethyl-4,5-benzospiro[2,4]hepta-4,6-diene-1-carboxylic acid, m-phenoxybenzyl ester | 1.0 / 0.3 | 51 / 7 |
| 2,2-Dimethyl-4,5-benzospiro[2,4]hepta-4,6-diene-1-carboxylic acid, α-cyano-m-phenoxybenzyl ester | 0.1 / 0.03 | 61 / 12 |
| Chlorinated camphene plus the m-phenoxybenzyl ester (identified-above) | 20 + 1.0 | 95 |
| Methyl parathion plus the m-phenoxybenzyl ester (identified-above) | 1.0 + 0.3 | 99 |
| Methyl parathion plus the α-cyano-m-phenoxybenzyl ester (identified above) | 1.0 + 0.03 | 100 |
| Chlorinated camphene plus Methyl parathion plus The m-phenoxybenzyl ester | 0.6 + 0.3 + 1.0 | 95 |
| Chlorinated camphene plus Methyl parathion plus The α-cyano-phenoxybenzyl ester | 0.6 + 0.3 + 0.1 | 95 |
| Chlorinated camphene plus Methyl parathion plus Chlordimeform plus The α-cyano-m-phenoxybenzyl ester | 0.6 + 0.3 + 0.04 + 0.1 | 100 |
| Chlorinated camphene plus Chlordimeform plus The m-phenoxybenzyl ester | 12.5 + 25 + 0.25 | 80 |
| Chlordimeform plus | 100 | |

Table V-continued

| Effectiveness of Chemical Compositions for Controlling Bean Apids (*Aphid fabae Scopoli*) | | |
|---|---|---|
| Chemical or Composition | Concentration ppm | % Mortality |
| The m-phenoxybenzyl ester | + 1.0 | 100 |
| Chlorinated camphene plus | 12.5 + | |
| Chlordimeform plus | 25 + | 80 |
| The α-cyano-m-phenoxybenzyl ester | 0.025 | |
| Malathion plus | 10 + | 95 |
| The m-phenoxybenzl ester | 1.0 | |
| Malathion plus | 10 + | 100 |
| The α-cyano-m-phenoxybenzyl ester | 0.1 | |
| Azinphos-methyl plus | 1.5 + | 100 |
| The α-cyano-m-phenoxybenzyl ester | 0.05 | |
| Carbaryl plus | 1.0 + | 100 |
| The m-phenoxybenzyl ester | 1.0 | |
| Carbaryl plus | 1.0 + | 90 |
| The α-cyano-m-phenoxybenzyl ester | 0.1 | |

EXAMPLE 18

Evaluation of Test Compositions for the Control of Southern Armyworms (*Spodoptera eridania* (Cramer))

A treated primary leaf of a Sieva lima bean plant is placed in a 9.0 cm petri dish with moist Whatman #1 filter paper on the bottom and containing 10, third-instar southern armyworm larvae. The dish is covered and held in a room maintained at 26° C and 30% relative humidity. After 3 days, all petri dishes are examined and mortality counts are made. Data obtained are reported in Table VI below.

EXAMPLE 19

Evaluation of Test Compositions for the Control of Tarnished Plant Bug (*Lygus Lineolaris* (Palisot de Beauvois))

A treated primary leaf of a Sieva lima bean plant is placed in an 8 oz waxed cup containing a 2 inch dental wick saturated with water and 10 adult tarnished plant bugs. The cup is covered with a clear plastic lid and held in a room maintained at 26° C and 30% relative humidity. After 3 days, the leaves in the cups are examined and mortality counts are made. Data obtained are reported in Table VII below.

Table VI

| Effectiveness of Test Compositions for Controlling Southern Armyworms (*Spodotera eridana*) | | | |
|---|---|---|---|
| Compound or Composition | Concentration ppm | % Mortality | % Feeding Damage |
| Chlorinated camphene | 30 | 40 | 100 |
| Methyl parathion | 10 | 40 | 100 |
| Chlordimeform | 1000 | 70 | 55 |
| " | 300 | 40 | 80 |
| Carbaryl | 30 | 0 | 100 |
| 2,2-Dimethyl-4,5-benzospiro[2,4]- | 6 | 50 | 50 |
| hepta-4,6-diene-1-carboxylic acid, | 3 | 80 | |
| m-phenoxybenzyl ester | 1.5 | 0 | 100 |
| 2,2-Dimethyl-4,5-benzospiro[2,4]hepta- | 3 | 66 | 12 |
| 4,6-diene-1-carboxylic acid, α-cyano- | 1.5 | 10 | 15 |
| phenoxybenzyl ester | 1 | 0 | 43 |
| Chlordimeform plus | 1000 | | |
| The α-cyano-m-phenoxybenzyl ester (identified-above) | + 1 | 100 | 1 |
| Chlordimeform plus | 250 | | |
| The m-phenoxybenzyl ester (identified above) plus | + 0.75 | 90 | 15 |
| chlorinated camphene | + 25.0 | | |
| Chlorinated camphene plus | 30 | | |
| Methyl parathion plus | + 15 | | |
| Chlordimeform plus | + 1.9 | 100 | 5 |
| The α-cyano-m-phenoxybenzyl ester | + 3 | | |
| Malathion plus | 100 | | |
| The α-cyano-m-phenoxybenzyl ester | + 3 | 90 | 5 |
| Carbaryl plus | 30 | | |
| The m-phenoxybenzyl ester | + 3 | 100 | 10 |

Table VII

Effectiveness of Test Compositions for Controlling Tarnished Plant Bugs
(*Lygus lineaolaris* (Palisot de Beauvois))

| Chemical or Composition | Concentration ppm | % Mortality |
|---|---|---|
| Methyl parathion | 0.3 | 40 |
| Chlorinated camphene | 10 | 50 |
| 2,2-Dimethyl-4,5-benzospiro[2,4]hepta-4,6-diene-1-carboxylic acid, m-phenoxybenzyl ester | 30 | 42 |
| 2,2-Dimethyl-4,5-benzospiro[2,4]hepta-4,6-diene 1-carboxylic acid, α-cyano-m-phenoxybenzyl ester | 10 | 47 |
| Methyl parathion plus The m-phenoxybenzyl ester (identified above) | 0.3 + 30 | 100 |
| Chlorinated camphene plus Methylparathion plus | 1.5 + 0.75 | 90 |
| The α-cyano-m-phenoxybenzyl ester (identified above) | + 5 | |

I claim:

1. An insecticidal composition comprising (i) about 1 to 100 ppm of a phenoxybenzyl ester of a spirocarboxylic acid having a formula

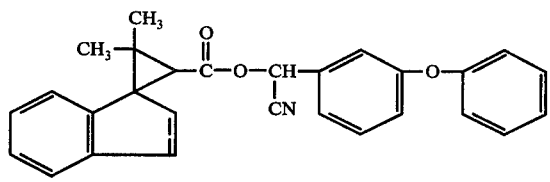

wherein ≈≈≈ represents a single or a double bond; the optical or geometric isomers thereof; and (ii) about 1000 ppm N'-(4-chloro-o-tolyl)-N,N-dimethylformamidine.

2. A composition according to claim 1 wherein the phenoxybenzyl ester is 2,2-dimethyl-4,5-benzospiro[2,4]hepta-4,6-diene-1-carboxylic acid, α-cyano-m-phenoxybenzyl ester.

3. An insecticidal composition comprising (1) about 1 ppm of a phenoxybenzyl ester of a spirocarboxylic acid having a formula

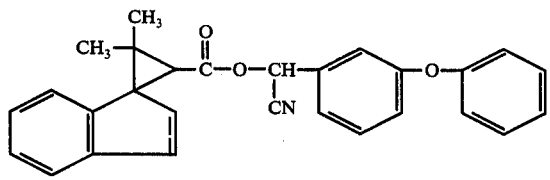

wherein ≈≈≈ represents a single or a double bond; the optical or geometric isomers thereof; (2) about 15 ppm O,O-di-methyl-O-p-nitrophenylphosphorothioate; (3) about 30 ppm chlorinated camphene; and (4) about 1.8 ppm N'-(4-chloro-o-tolyl)-N,N-dimethylformamidine.

4. A composition according to claim 3 wherein the spirocarboxylic acid is 2,2-dimethyl-4,5-benzospiro[2,4]hepta-4,6-diene-1-carboxylic acid, α-cyano-m-phenoxybenzyl ester.

5. A method for the control for insect pests comprising applying to the insects habitat, their food supply or their breeding sites, an insecticidally effective amount of a composition comprising (1) about 1 ppm of a phenoxybenzyl ester of a spirocarboxylic acid having a formula

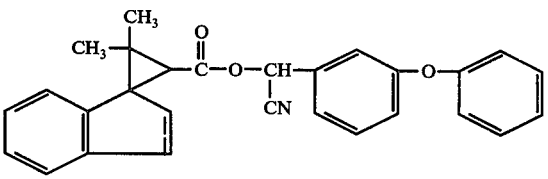

wherein ≈≈≈ represents a single or double bond; the optical or geometric isomers thereof; (2) about 30 ppm chlorinated camphene; (3) about 15 ppm O,O-dimethyl-O-p-nitrophenyl phosphorothioate; and (4) about 1.8 ppm N'-(4-chloro-o-tolyl)-N,N-dimethylformamidine.

6. A method according to claim 5 for the control of *Lepidopterous, Hemipterous* and *Coleopterous* wherein the spirocarboxylic acid is 2,2-dimethyl-4,5-benzospiro[2,4]hepta-4,6-diene-1-carboxylic acid, α-cyano-m-phenoxybenzyl ester and the composition is applied in a sufficient amount to provide from 1 to 5 oz per acre of the spirocarboxylic acid derivative and from 0.25 to 4 lbs per acre of chlorinated camphene; O,O-dimethyl-O-p-nitrophenylphosphorothioate; and N'-(4-chloro-o-tolyl)-N,N-dimethylformamidine.

7. A method for the control for insect pests comprising applying to the insects habitat, their food supply or their breeding sites, a composition comprising (i) about 1 to 100 ppm of a phenoxybenzyl ester of a spirocarboxylic acid having the formula

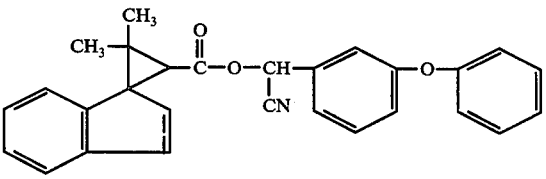

wherein ≈≈≈ represents a single or double bond; the optical or geometric isomers thereof; and (ii) about 1000 ppm N'-(4-chloro-o-tolyl) N,N-dimethylformamidine.

8. A method according to claim 7 wherein the spirocarboxylic acid derivative is 2,2-dimethyl-4,5-benzospiro[2,4]hepta-4,6-diene-1-carboxylic acid, α-cyano-m-phenoxybenzyl ester.

9. A method for the control of insect pests according to claim 5 in cotton crops.

* * * * *